United States Patent
Neumann

(10) Patent No.: US 11,587,685 B2
(45) Date of Patent: Feb. 21, 2023

(54) METHODS AND SYSTEMS FOR PHYSIOLOGICALLY INFORMED ZOOLOGICAL SELECTION

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 471 days.

(21) Appl. No.: 16/778,769

(22) Filed: Jan. 31, 2020

(65) Prior Publication Data

US 2021/0241921 A1 Aug. 5, 2021

(51) Int. Cl.
*G16H 50/70* (2018.01)
*G16H 10/60* (2018.01)
*G06K 9/62* (2022.01)
*G06N 20/00* (2019.01)
*G06N 20/10* (2019.01)

(52) U.S. Cl.
CPC .............. *G16H 50/70* (2018.01); *G06K 9/623* (2013.01); *G06K 9/6215* (2013.01); *G06K 9/6218* (2013.01); *G06N 20/00* (2019.01); *G16H 10/60* (2018.01); *G06N 20/10* (2019.01)

(58) Field of Classification Search
CPC ........ G16H 10/00–80/00; G06N 3/00–99/007; G06K 1/00; G06K 2215/111
See application file for complete search history.

(56) References Cited

U.S. PATENT DOCUMENTS

| 2008/0065473 A1 | 3/2008 | Stroman et al. |
| 2018/0078214 A1 | 3/2018 | Flanagan et al. |
| 2019/0183096 A1 | 6/2019 | Moreno et al. |
| 2019/0209022 A1 | 7/2019 | Sobol et al. |

(Continued)

FOREIGN PATENT DOCUMENTS

| JP | 2015076082 A | * | 4/2015 |
| WO | 2019143714 | | 7/2019 |

OTHER PUBLICATIONS

Abramson et al., "The Relationship between Personality Match and Pet Satisfaction among Dog Owners," Anthrozoos a Multidisciplinary Journal of the Interactions of People & Animals • Jun. 2013 vol. 26, Issue 3 (Year: 2013).*

(Continued)

*Primary Examiner* — Jonathon A. Szumny
(74) *Attorney, Agent, or Firm* — Caldwell Intellectual Property Law

(57) ABSTRACT

A system for physiologically informed zoological selection. The system includes a computing device configured to record a user biological extraction profile. A computing device receives condition state training data and calculates a plurality of condition vector outputs for a user biological extraction profile utilizing a first clustering algorithm. A computing device selects a characteristic condition vector output. A computing device receives zoological training data and calculates a plurality of animal vector outputs utilizing a second clustering algorithm. A computing device creates a ranked listing of animals utilizing a plurality of animal vector outputs.

20 Claims, 5 Drawing Sheets

(56) References Cited

U.S. PATENT DOCUMENTS

2019/0385711 A1   12/2019   Shriberg et al.

OTHER PUBLICATIONS

Fratkin et al., "Personality Consistency in Dogs: A Meta-Analysis," PLOS One Jan. 2013 | vol. 8 | Issue 1. (Year: 2013).*
Manik Soni, How to Make AI That Classifies Dog Breeds, Website Article, Jul. 18, 2018 https://hackernoon.com/ai-classifies-15000-years-old-animal-dog-the-easiest-way-cd6619cd4d59.
Saqib Shah, Hounds Good Your iPhone or Android phone can now identify dog breeds in photos you take, Website Article, Apr. 18, 2018 https://www.thesun.co.uk/tech/6035870/google-photos-dog-recognition-iphone-android/.

* cited by examiner

METHODS AND SYSTEMS FOR PHYSIOLOGICALLY INFORMED ZOOLOGICAL SELECTION

FIELD OF THE INVENTION

The present invention generally relates to the field of artificial intelligence. In particular, the present invention is directed to methods and systems for physiologically informed zoological selection.

BACKGROUND

Zoological selection can frequently be challenging due to the unpredictable relationships that subsequently develop after acquisition of an animal. This can be further hampered by high unique individual situations that can affect the compatibility and tolerability of animals. Currently, there remains to be seen a way of utilizing physiological information to inform animal selection and tolerability.

SUMMARY OF THE DISCLOSURE

A system for physiologically informed zoological selection, the system comprising a computing device. The computing device configured to record a user biological extraction profile wherein the user biological extraction profile contains at least an element of user physiological data and a user symptom complaint datum. The computing device configured to receive condition state training data wherein condition state training data further comprises a plurality of user biological extraction profiles and a plurality of correlated conditions. The computing device configured to calculate a plurality of condition vector outputs for the user biological extraction profile utilizing the condition state training data and a first clustering algorithm. The computing device configured to select a characteristic condition vector output from the plurality of condition vector outputs. The computing device configured to receive zoological training data wherein zoological training data further comprises a plurality of conditions and a plurality of correlated animals. The computing device configured to calculate a plurality of animal vector outputs utilizing the selected characteristic condition vector output, the zoological training data and a second clustering algorithm. The computing device configured to create a ranked listing of animals utilizing the plurality of animal vector outputs.

A method of physiologically informed zoological selection. The method includes recording by a computing device a user biological extraction profile wherein the user biological extraction profile contains at least an element of user physiological data and a user symptom complaint datum. The method includes receiving by the computing device condition state training data wherein condition state training data further comprises a plurality of user biological extraction profiles and a plurality of correlated conditions. The method includes calculating by the computing device a plurality of condition vector outputs for the user biological extraction profile utilizing the condition state training data and a first clustering algorithm. The method includes selecting by the computing device a characteristic condition vector output from the plurality of condition vector outputs. The method includes receiving by the computing device zoological training data wherein zoological training data further comprises a plurality of conditions and a plurality of correlated animals. The method includes calculating by the computing device a plurality of animal vector outputs utilizing the selected characteristic condition vector output, the zoological training data and a second clustering algorithm. The method includes creating by the computing device a ranked listing of animals utilizing the plurality of animal vector outputs.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for physiological informed zoological selection. In an embodiment, a computing device receives information pertaining to a user that includes a user biological extraction profile and a user symptom complaint datum. A computing device may convert one or more inputs relating to a user into a series of one or more vector outputs represented in n-dimensional space. A computing device utilizes training data and a first clustering algorithm to generate a plurality of correlated conditions. A computing device selects a characteristic condition vector output and utilizes additional training data and a second clustering algorithm to output a plurality of correlated animals. A computing device calculates animal vector outputs and generates a ranked listing of animals.

Figure 1:
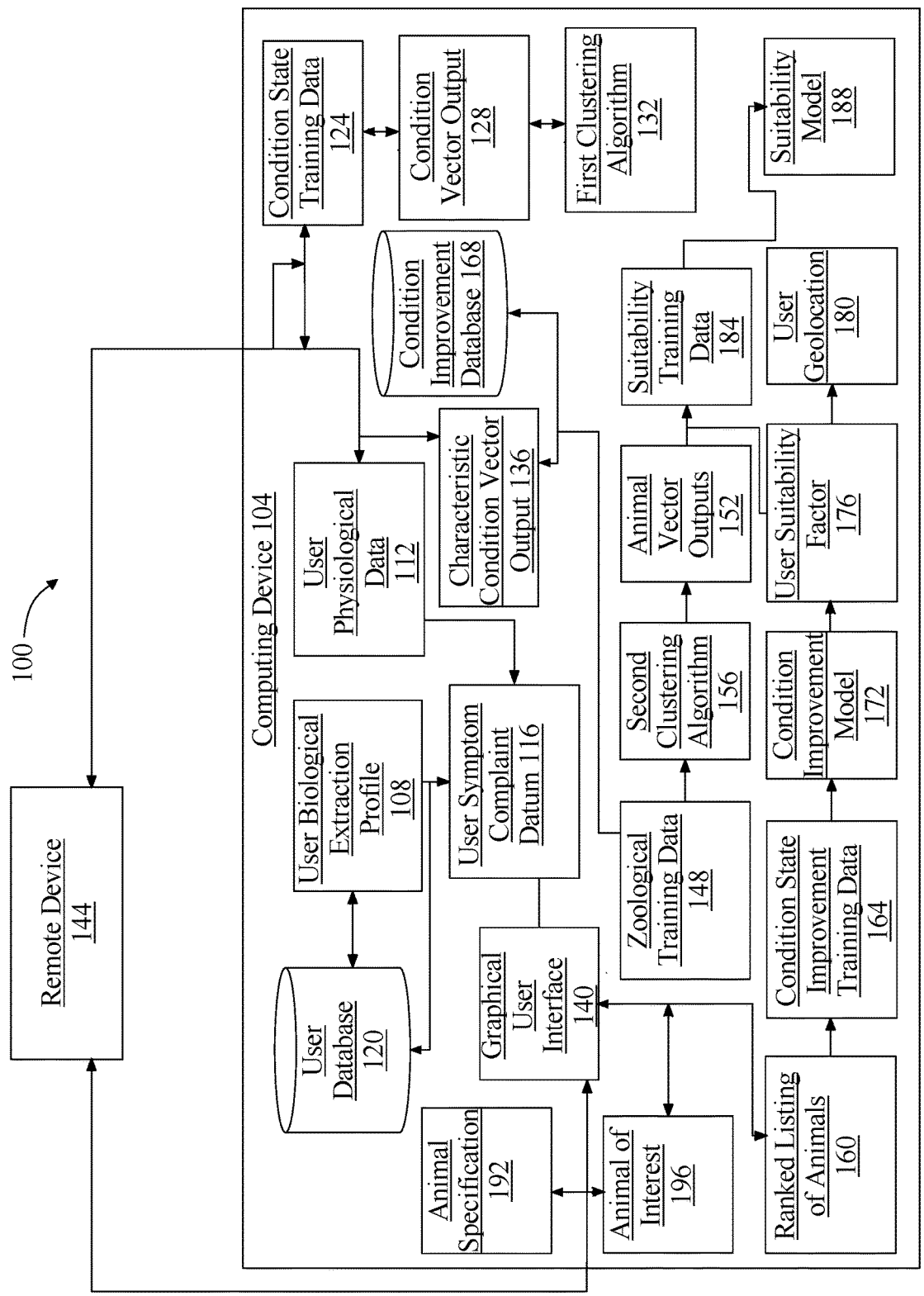
FIG. 1 is a block diagram illustrating an exemplary embodiment of a system for physiologically informed zoological selection.

Referring now to FIG. 1, an exemplary embodiment of a system 100 for physiologically informed zoological selection is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 is configured to record a user biological extraction profile 108. A "user biological extraction profile," as used in this disclosure, is a collection of data entries pertaining to a user. A user biological extraction profile 108 contains at least an element of user physiological data 112. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile*, *cryptosporidium* species, *Cyclospora cayetanensis*, *Cryptosporidium* EIA, *Dientamoeba fragilis*, *Entamoeba histolytica*, *Escherichia coli*, *Entamoeba histolytica*, *Giardia*, *H. pylori*, *Candida albicans*, *Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, *Proteobacteria* species, *Verrumicrobia* species, *Actinobacteria* species, *Fusobacteria* species, Cyanobacteria species and the like. Archaea may include methanogens such as *Methanobrevibacter smithies'* and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, *Anaerotruncus colihominis*, bacteriology, *Bacteroides vulgates'*, *Bacteroides-Prevotella*, *Barnesiella* species, *Bifidobacterium longarm*, *Bifidobacterium* species, *Butyrivbrio crossotus*, *Clostridium* species, *Collinsella aerofaciens*, fecal color, fecal consistency, *Coprococcus eutactus*, *Desulfovibrio piger*, *Escherichia coli*, *Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, user biological extraction profile 108 contains a user symptom complaint datum 116. A "user symptom complaint datum," as used in this disclosure, is an element of data describing any evidence of disease in a user's body. A user symptom complaint datum 116 may include a description of any body symptom that a user may be experiencing. A "body symptom" as used in this disclosure, includes any physical or mental feature which is regarded as indicating a condition and/or disease. Physical and/or mental feature may include any sign and/or symptom relevant to a potential medical condition and/or symptom. Physical and/or mental feature may include a sign such as clubbing on fingernails or a symptom such as mental fatigue. Body symptom may include dizziness, fever, tiredness, sleepiness, nausea, shortness of breath, abdominal pain, hearing loss, inability to pass urine, profusive sweating, alopecia, and the like. Body symptom may be located to one particular location of the body such as a body symptom that includes a description of pelvis pain or blurry vision in a user's left eye. Body symptom may be limited to one or more body systems such as a cardiovascular arrhythmia or abdominal bloating and fecal incontinence. Body symptom may be apparent as indicating to a user a particular condition and/or disease such as when a patient experiences a body symptom such as blood loss from a flesh wound. Body symptom may not be apparent as indicating to a user a particular condition and/or disease such as when a patient experiences a body symptom such as tiredness due to a thyroid condition which the user believes is simply due to being overly fatigued. Body symptom may include a remitting symptom, such as when symptoms improve or resolve completely. For instance and without limitation, symptoms of a common cold such as stuffy nose, headache, sneezing, and congested sinuses may occur for several days and then resolve with or without treatment. Body symptom may include a chronic symptom, such as when symptoms are long-lasting and recurrent. For example, foot pain experienced as a result of diabetic neuropathy may be long-lasting symptoms experienced throughout the duration of a user having diabetes. Body symptom may include a chronic symptom such as fatigue and loss of interest and pleasure in activities. Body symptom may include a relapsing symptom, which may include a symptom that occurred in the past at some other point in time, resolved, and then returned. For example, symptoms of depression may not occur for years at a time but then may return without notice. User symptom complaint datum 116, may include a description of a body symptom that a user may be currently experiencing and/or recently experienced. For example, user symptom complaint datum 116 may include a description of a blood coming out of a nostril or low back pain after sitting or a description of jaw pain that occurs upon waking. Body symptom may include a description of a health state such as a female who is currently pregnant or a description of a condition such as ulcerative colitis that is currently in remission.

With continued reference to FIG. 1, computing device 104 may store information relating to a user biological extraction profile 108 in a user database 120 as described below in more detail. User database 120 may be implemented, without limitation, as a relational database, a key-value retrieval datastore such as a NOSQL database, or any other form or structure for use as a datastore that a person skilled in the art would recognize as suitable upon review of the entirety of this disclosure.

With continued reference to FIG. 1, computing device 104 is configured to receive condition state training data 124. "Training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, "condition state training data," as used in this disclosure, is training data that includes a plurality of user biological extraction profiles 108 and a plurality of correlated conditions. A "condition," as used in this disclosure, is any data describing the presence and/or absence of any disease, syndrome, lesion, disorder, illness, infection, epidemic, injury, and/or medical state. For instance and without limitation, a condition may indicate a syndrome such as irritable bowel syndrome or encephalopathic syndrome. In yet another non-limiting example, a condition may indicate a disease such as hypertension or coronary artery disease. In yet another non-limiting example, a condition may indicate an infection such as cellulitis or a urinary tract infection. In yet another non-limiting example, a condition may indicate an illness such as small intestinal bacterial overgrowth (SIBO), or a tension headache.

With continued reference to FIG. 1, computing device 104 is configured to calculate a plurality of condition vector output 128. A "condition vector output," as used in this disclosure, is a data structure representing a condition. Proximity of a user biological extraction profile vector to a condition vector output may indicate the probability that a user has a given condition. A condition vector output 128 may include and/or be an "n" n-tuple of values, where n is at least two values. Each value of n-tuple of values may represent a measurement or other quantitative value associated with a given category of data, or attribute. A condition vector output 128 may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance be advantageous where each vector represents a weighing of a characteristic condition vector output, and/or is to be compared to such a weighing of a characteristic condition vector output. A condition vector output 128 may contain a label, identifying a condition associated with a particular condition vector output 128. For example, a first condition vector output 128 intended for hypertension may be reflected in a label identifying the first condition vector output 128 as representing hypertension, while a second condition vector output 128 intended for allergic rhinitis may be reflected in a label identifying the second condition vector output 128 as representing allergic rhinitis. In an embodiment, a label may identify a particular stage of a condition that may reflect the severity of the condition. For example, a label may identify a condition vector output 128 as indicating stage two ulcerative colitis where there is a significant risk of complications, as compared to a label that may identify a condition vector output 128 as indicating stage one ulcerative colitis where there is minimal severity and minimal risk of complications.

With continued reference to FIG. 1, computing device 104 calculates a plurality of condition vector outputs 128 utilizing condition state training data 124 and a first clustering algorithm 132. A "clustering algorithm," as used in this disclosure, is a series of one or more calculations that groups a set of objects in such a way that objects in the same group or cluster are more similar to each other than to those in other groups or clusters. A clustering algorithm may include generating one or more clustering models. Clustering models may include for example, connectivity models such as hierarchical clustering. Clustering models may include for example, centroid models such as k-means algorithm. Clustering models may include for example, distribution models such as multivariate normal distributions using an expectation-maximization algorithm. Clustering models may include for example, density models such as density-based spatial clustering of applications with noise (DBSCAN) or ordering points to identify a clustering structure (OPTICS). Clustering models may include for example, subspace models such as bi-clustering. Clustering models may include for example, group models. Clustering models may include graph-based models such as highly connected subgraphs (HCS) clustering algorithm. Clustering models may include signed graph models. Clustering models may include neural models such as an unsupervised neural network With continued reference to FIG. 1, clustering algorithms and/or clustering models may be generated as hard and/or soft clusters. Clustering algorithms and/or clustering models may include hard clusters whereby each object belongs to a cluster or not. Clustering algorithms and/or clustering models may include soft clustering whereby each object may belong to each cluster to a certain degree. Clustering algorithms and/or clustering models may include strict partitioning clustering where each object belongs to exactly one cluster. Clustering algorithms and/or clustering models may include strict partitioning clustering with outliers where objects can also belong to no cluster and may be considered outliers. Clustering algorithms and/or clustering models may include overlapping clustering where objects may belong to more than one cluster. Clustering algorithms and/or clustering models may include hierarchical clustering where objects that belong to a child cluster may also belong to the parent cluster. Clustering algorithms and/or clustering models may include subspace clustering.

With continued reference to FIG. 1, computing device 104 is configured to select a characteristic condition vector output 136 from a plurality of condition vector outputs 128. An "characteristic condition vector output," as used in this disclosure, is a "first guess" by computing device 104 at the nearest vector in the feature space containing a user biological extraction profile 108. Characteristic condition vector output 136 may contain a label, indicating identifying a condition associated with a particular characteristic condition vector output 136. For example, a first characteristic condition vector output 136 associated with a condition such as generalized anxiety disorder may contain a label indicating generalized anxiety disorder while a second characteristic condition vector output 136 such as irritable bowel syndrome may contain a label indicating irritable bowel syndrome. Computing device 104 may return a single matching entry or a plurality of matching entries. When a plurality of matching entries is returned, computing device 104 may derive characteristic condition vector output from plurality of matching entries by aggregating matching entries; aggregation may be performed using any suitable method for aggregation, including component-wise addition followed by normalization, component-wise calculation of arithmetic means, or the like. Computing device 104 may select a characteristic condition vector output by weighing degree of proximity and a user input together. In an embodiment, this may be performed utilizing one or more additional machine-learning algorithms and/or machine-learning models such as by generating a loss function. Computing device 104 may include a user input containing a specified condition as a vector, and compare it to one or more clusters. Computing device 104 may select a characteristic condition vector output by picking a k most probable vector output using any additional data such as a user symptom complaint datum or a user input containing a specified condition.

With continued reference to FIG. 1, computing device 104 may select a characteristic condition vector output 136 based on user input. Computing device 104 may receive a user input containing a specified condition. A "user input," as used in this disclosure, is any data generated by a user. Computing device 104 may include a graphical user interface 140 on which a user may enter a specified condition. A "specified condition," as used in this disclosure, is the identification of any condition identified as pertaining to a user identified by the user. A condition may pertain to a user when a user has been previously diagnosed with a condition. For example, a user may self-report a condition such as a grass allergy that the user was diagnosed with six years earlier by a medical doctor. A condition may pertain to a user when a user is currently undergoing treatment for a particular condition. For example, a user may self-report a condition such as mold toxicity for which the user is currently undergoing treatment. A condition may pertain to a user when a user suspects the user may have and/or may be diagnosed with a particular condition. For example, a user may believe that he or she has a condition such as narcolepsy because he or she experiences symptoms that align with narcolepsy such as excessive daytime sleepiness, disturbed nighttime sleep and memory problems. In yet another non-limiting example, a user may believe that the user has a particular condition because a condition such as diabetes tends to occur in the user's family and the user has started to experience symptoms of diabetes including increased thirst, daytime sleepiness, and increased urination. Graphical user interface 140 may include, without limitation, a form or other graphical element having display fields, where one or more elements of information may be displayed. Graphical user interface 140 may include sliders or other use inputs that may permit a user to select a particular condition. In an embodiment, a user may select a condition the user has been previously diagnosed with or that the user believes he or she may have. Graphical user interface 140 may include free form textual fields where a user can type in or enter one or more conditions that may be of pertinence to the user.

With continued reference to FIG. 1, computing device 104 may receive a user input containing a specified condition from a remote device 144. Remote device 144 may include without limitation, a display in communication with computing device 104, where a display may include any display as described herein. Remote device 144 may include an additional computing device, such as a mobile device, laptop, desktop, computer and the like. A user input containing a specified condition may be transmitted to computing device 104 utilizing any network methodology as described herein.

With continued reference to FIG. 1, computing device 104 identifies a condition vector output 128 related to a specified condition. A condition vector output 128 may be related to a specified condition when the specified condition matches a condition identified by a condition vector output 128 and/or the condition vector output 128 label. For instance and without limitation, computing device 104 may receive a user input containing a specified condition such as chronic obstructive pulmonary disease (COPD), which the user may have been previously diagnosed with by the user's medical doctor. In such an instance, computing device 104 may identify a condition vector output 128 for chronic obstructive pulmonary disease (COPD). In yet another non-limiting example, computing device 104 may receive a user input containing a specified condition such as advanced Alzheimer's disease and computing device 104 may identify a condition vector output 128 for advanced Alzheimer's disease.

With continued reference to FIG. 1, computing device 104 may select a characteristic condition vector output 136 utilizing a user biological extraction profile 108. Computing device 104 may convert a user biological extraction profile 108 to a vector output. Computing device 104 may convert a user biological extraction profile 108 to a vector output by transforming the user biological extraction profile 108 into n-dimensional space using an axis per category of value represented in n-tuple of values. This may include calculating a "n" n-tuple of values, for the user biological extraction profile 108 as described above in more detail. Computing device 104 converts a user biological extraction profile 108 to a biological extraction profile vector output. Computing device 104 maps a user biological extraction profile 108 vector output in relation to the plurality of condition vector output 128. Mapping may include measuring a distance in n-dimensional space between a user biological extraction profile 108 vector output and the plurality of condition vector output 128. Computing device 104 locates a condition vector output 128 closest to a user biological extraction profile 108 vector output. Computing device 104 may locate a condition vector output 128 closest to a user biological extraction profile 108 vector output by comprising distances between the user biological extraction profile 108 vector output and the plurality of condition vector output 128. In an embodiment, computing device 104 may select a condition vector output 128 as the characteristic condition vector output 136 that has the shortest distance and is the closest to the biological extraction profile vector output.

With continued reference to FIG. 1, computing device 104 may select a distance metric. In an embodiment, computing device 104 may utilize Euclidean distance which may measure distance by subtracting the distance between a user biological extraction profile 108 vector output and a condition vector output 128. In an embodiment, Euclidean distance may be calculated by a formula represented as:

$$E(x, y) = \sqrt{\sum_{i=0}^{n}(xi - yi)^2}.$$

In an embodiment, computing device 104 may utilize metric distance of cosine similarity which may calculate distance as the difference in direction between two vectors which may be represented as: similarity=cos θ=A×B÷∥A∥∥B∥. In an embodiment, distance may be measured utilizing one or more other measurements of distance, including for example Manhattan distance, Minkowski distance, Mahalanobis distance, and/or Jaccard distance.

With continued reference to FIG. 1, selecting a characteristic condition vector output 136 may include displaying condition vectors to a user. Computing device 104 may display on a graphical user interface 140 a plurality of condition vector output 128. Graphical user interface 140 may include any of the graphical user interface 140 as described herein. Computing device 104 may receive a user command selecting a condition vector output 128 from a plurality of condition vector output 128. A user command may include a selection from a plurality of condition vector output 128. For instance and without limitation, computing device 104 may display on a graphical user interface 140 located on computing device 104 a plurality of condition vector output 128 that include a first condition vector output 128 for arthritis, a second condition vector output 128 for hypertension, a third condition vector output 128 for asthma, a fourth condition vector output 128 for chronic bronchitis, and a fifth condition vector output 128 for coronary heart disease. In such an instance, computing device 104 may receive a user command selecting the third condition vector output 128 for asthma. In an embodiment, a user may enter a user command selecting a condition vector output 128 for any of the reasons as described above in reference to generating a specified condition. For example, a user may have been previously diagnosed with a particular condition and may select a condition vector output 128 that matches the particular condition the user was previously diagnosed with. In yet another non-limiting example, a user may have a suspicion that the user suffers from a particular condition and the user may select a condition vector output 128 for the particular condition that the user suspects the user suffers from.

With continued reference to FIG. 1, computing device 104 is configured to receive zoological training data 148. "Zoological training data," as used in this disclosure, is training data that includes a plurality of conditions and a plurality of correlated animals. "Animals" as used in this disclosure, include any domestic or tamed animal kept for companionship or pleasure. An animal may include a pet kept in one's house or one one's property. For instance and without limitation, an animal may include a rabbit, a cat, a dog, a ferret, a fish, a sugar glider, a bird, a turtle, a guinea pig, a hamster, a hedgehog, a goat, a horse, a gerbil, a chinchilla, a mouse, a rat, a reptile, a llama, a sheep, a tortoise, a common iguana, a lizard, a bearded dragon, cattle, a parrot, an amphibian, a rodent, a gecko, a puppy, a mammal, saltwater fish, a snake, and the like.

With continued reference to FIG. 1, computing device 104 is configured to calculate a plurality of animal vector output 152 utilizing a selected characteristic condition vector output, zoological training data 148, and a second clustering algorithm. An "animal vector output," as used in this disclosure, is a data structure representing a quantitative measure of an animal and any associated attributes and/or health benefits of the animal. An animal vector output 152 may include a label, identifying a particular animal associated with a particular animal vector output 152. An animal vector output 152 may include information relating to one or more biological features of an animal. Biological features may include information pertaining to a kingdom, phylum, class, order, family, genus, and/or species. For instance and without limitation, an animal vector output 152 may specify a cat as belonging to *Felis* genus and *F. catus* species. Computing device 104 may calculate a plurality of animal vector output 152 utilizing a second clustering algorithm 156. Second clustering algorithm 156 may include any clustering algorithm suitable for use as first clustering algorithm 132 as described above.

With continued reference to FIG. 1, computing device 104 is configured to create a ranked listing of animals 160 utilizing a plurality of animal vector output 152. A "ranked listing of animals," as used in this disclosure, is a data structure that contains a list of animals ranked by in an order specifically generated for a user. In an embodiment, animals may be ranked based on tolerability and suitability for a user. For example, a ranked listing of animals 160 may indicate that a cat is most suitable and tolerable for a user, followed by a fish that is the second most suitable and tolerable for the user, and lastly a hamster that is that is the third most suitable and tolerable for the user.

With continued reference to FIG. 1, ranked listing of animals 160 may be generated using one or more machine-learning algorithms. Computing device 104 may receive condition state improvement training data 164. "Condition state improvement training data 164," as used in this disclosure, is training data that includes a plurality of conditions and a plurality of correlated condition improvement components. A "condition improvement component," as used in this disclosure, is data identifying any treatment that ameliorates a given condition. A treatment may include the use drugs, exercise programs, dietary regimens, fitness habits, health habits, tasks, chores, and the like that may improve and/or cure a condition. For instance and without limitation, a condition such as obesity may be associated with a condition improvement component such as walking. In yet another non-limiting example, a condition such as hypertension may be associated with a condition improvement component such as meditation. A condition may be associated with one or more condition improvement components. For example, obesity may be associated with any condition improvement component that includes cardiovascular exercise including walking, running, jogging, biking, swimming, aerobics, dancing, cross country skiing, and kickboxing. In yet another non-limiting example, a condition such as osteoarthritis may be associated with condition improvement components that include strength exercise, cardiovascular exercise, medication, and meditation. In an embodiment, one or more condition improvement components may be stored in a condition improvement database 168, as described below in more detail. Condition improvement database 168 may be implemented as any data structure suitable for use as user database 120 as described above.

With continued reference to FIG. 1, computing device 104 is configured to generate a condition improvement model 172. A "condition improvement model," as used in this disclosure, is a machine-learning model that utilizes condition vectors as an input and outputs condition improvement components. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 1, a machine learning process, also referred to as a machine-learning algorithm, is a process that automatedly uses training data and/or a training set as described above to generate an algorithm that will be performed by a computing device 104 and/or module to produce outputs given data provided as inputs; this is in contrast to a non-machine learning software program where the commands to be executed are determined in advance by a user and written in a programming language.

Continuing to refer to FIG. 1, machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

With continued reference to FIG. 1, supervised machine-learning processes may include classification algorithms, defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithms may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

With continued reference to FIG. 1, computing device 104 identifies animal vectors linked to condition improvement components. An animal vector may be linked to a condition improvement component when caring for and having an animal associated with an animal vector is attributed to and/or results in a user partaking in a condition improvement component. For instance and without limitation, an animal vector associated with an animal such as a dog may be attributed to a condition improvement component that includes increased movement and increased exercise as having a dog requires taking a dog out for frequent walks and picking up after a dog if a dog makes a mess or causes toys to become displaced. In yet another non-limiting example, an animal vector associated with an animal such as a rabbit may be associated with a condition improvement component that includes reduced anxiety and greater sense of purpose as a rabbit can serve as a companion and reduce loneliness. Computing device 104 may rank animal vectors linked to output condition improvement components. For example, computing device 104 may rank an animal vector for a puppy higher than an animal vector for a fish for a user with a condition such as rheumatoid arthritis, as having a puppy will encourage the user to engage in more movement as well as help in preventing depression that can occur to users with autoimmune conditions as a puppy can serve as a companion and can interact more with a user as compared to a fish.

With continued reference to FIG. 1, creating a ranked listing of animals 160 may include identifying animals that may be suitable for a user. Computing device 104 may identify a user suitability factor 176. A "user suitability factor," as used in this disclosure, is data describing any factor that may impact a user's ability to care for and/or own an animal. A factor may include how much time a user is willing to spend looking after and taking care of an animal, how much money a user has to spend taking care of an animal, how much space and/or land that a user has to take care of an animal, allergies to certain animals, types of animals that a user likes, types of animals that a user dislikes, and the like. In an embodiment, computing device 104 may receive a user suitability factor 176 from a user entry entered on a graphical user interface 140. In an embodiment, computing device 104 may receive a user suitability factor 176 from a network transmission received from a remote device 144. For example, a user suitability factor 176 may indicate that a user lives in a city and does not own a backyard that could house larger animals such as horses and cattle. In an embodiment, a user suitability factor 176 may be identified as a function of a user geo-location 180. A "user geolocation," as used in this disclosure, is an identification of a real-world geographical location of a user. A user geolocation 180 may be obtained from a radar source, remote device 144 such as a mobile phone, and/or internet connected device location. An element of user geolocation 180 may include a global positioning system (GPS) of a user. An element of user geolocation 180 may include geographic coordinates that may specify the latitude and longitude of a particular location where a user is located. A user geolocation 180 may be utilized to identify a user suitability factor 176 by indicating animals that may or may not be suitable for a user to own based on the user geolocation 180. For example, a Siberian husky dog may not be suitable for a user who lives in Hawaii but may be suitable for a user who resides in Bangor, Me. In yet another non-limiting example, an animal that thrives in warm climates such as a mini-crocodile may not be suitable for a user who resides in Michigan but may be suitable for a user who resides in San Diego. In an embodiment, a user suitability factor 176 and/or a user geolocation 180 may be stored in user database 120.

With continued reference to FIG. 1, computing device 104 receives suitability training data. "Suitability training data," as used in this disclosure, is training data that includes a plurality of suitability factors and a plurality of correlated animals. Computing device 104 generates a suitability model 188 utilizing suitability training data. A "suitability model," as used in this disclosure, is a machine-learning model that utilizes suitability factors as inputs and outputs animal vectors. Computing device 104 maps a distance between a user suitability factor 176 and output animal vectors. Mapping a distance includes any of the distance mapping as described above. Mapping a distance may include calculating a distance between a user suitability factor 176 and output animal vectors. Distance may be calculated utilizing any of the distance measurements as described above. Computing device 104 ranks output animal vectors based on distance between user suitability factors and output animal vectors. For example, computing device 104 may rank an animal vector higher for an animal vector that is located a shorter distance away from a user suitability factor 176 as compared to an animal vector that is located a farther distance away from the user suitability factor.

With continued reference to FIG. 1, computing device 104 may create a ranked listing of animals 160 utilizing user input. Computing device 104 may receive from a remote device 144 at least an animal specification 192. An "animal specification," as used in this disclosure, is data describing a user's preference for a particular animal. A user's preference may indicate a particular group or class of animal. For example, a user's preference may indicate all dogs or all fish. A user's preference may indicate a particular breed or type of animal such as an English cocker spaniel or a Southern platy fish. In an embodiment, a user may indicate a preference for one or more animals such as any bird, turtle, hedgehog, or horse. A user's preference may indicate a particular group or class of animal that a user dislikes or is not interested in having as a pet. For example, an animal specification 192 may indicate that a user is interested in rabbits, ferrets, dogs, and chinchillas but not a cat or dog. In yet another non-limiting example, an animal specification 192 may indicate that a user is interested in dogs but only Labrador retrievers, pugs, and poodles but no other dogs and also the user is interested in birds but only parrots, finches, and an old world sparrow.

With continued reference to FIG. 1, computing device 104 may represent an animal specification 192 as a vector. Computing device 104 may represent in n-dimensional space using an axis per category of value represented in n-tuple of values, such that a vector has a geometric direction characterizing the relative quantities of attributes in the n-tuple as compared to each other. Computing device 104 calculates a distance between an animal specification 192 which may be represented as a vector output and a plurality of animal vector output 152. Distance may be calculated utilizing any of the distance measurements as described above in more detail. For instance and without limitation, computing device 104 may calculate distance between an animal specification 192 vector and an animal vector output 152 using Euclidean distance. Computing device 104 ranks an animal specification within the ranked listing of animals 160 as a function of a distance measurement. For instance and without limitation, computing device 104 may receive an animal specification 192 from a remote device 144 containing a user preference for a beagle dog. Computing device 104 may convert the animal specification 192 containing the user preference for a beagle dog into a vector output. Computing device 104 may then calculate a distance between the animal specification 192 vector output and a plurality of animal vector output 152. Computing device 104 may then rank the animal specification 192 containing the beagle dog within the ranked listing of animals 160 produced from the plurality of animal vector output 152.

With continued reference to FIG. 1, computing device 104 may identify an animal of interest 196 for a user. An "animal of interest," as used in this disclosure, is data describing an animal that a user may seek to consider as a pet, chosen by computing device 104. In an embodiment, computing device 104 may choose an animal of interest 196 using one or more machine-learning models. Machine-learning models may include any of the machine-learning models as described herein. In an embodiment, computing device 104 may identify an animal of interest 196 based on a user preference or user geolocation 180. For example, computing device 104 may identify an animal of interest 196 such as a snake for a user who resides in a metropolitan area of Alabama while computing device 104 may identify an Irish setter for a user who resides on a farm with plenty of open space in Montana. Computing device 104 may locate an animal vector output 152 related to an animal of interest 196. In an embodiment, an animal vector output may be related to an animal of interest 196 when interest when an animal of interest 196 matches an animal vector output. For instance and without limitation, an animal of interest 196 such as a hamster may be related to an animal vector output for a hamster. In an embodiment, an animal of interest 196 may be related to an animal vector output 152 when an animal of interest 196 belongs to the same group and/or classification of an animal vector output 152. For instance and without limitation, an animal of interest 196 such as a cocker spaniel may be related to an animal vector for a dog. In yet another non-limiting example, an animal of interest 196 such as a Siamese fighting fish may be related to an animal vector for a fish. Computing device 104 determines the compatibility of an animal of interest 196 utilizing a ranked listing of animals 160. Computing device 104 may evaluate the ranking of the located animal vector output 152 related to the animal of interest 196 and utilize that ranking to determine the compatibility of the animal of interest 196. In an embodiment, computing device 104 may display compatibility of animal of interest 196 on graphical user interface 140 located on computing device. In yet another non-limiting example, computing device 104 may transmit to remote device 144 compatibility of animal of interest 196.

Figure 2:
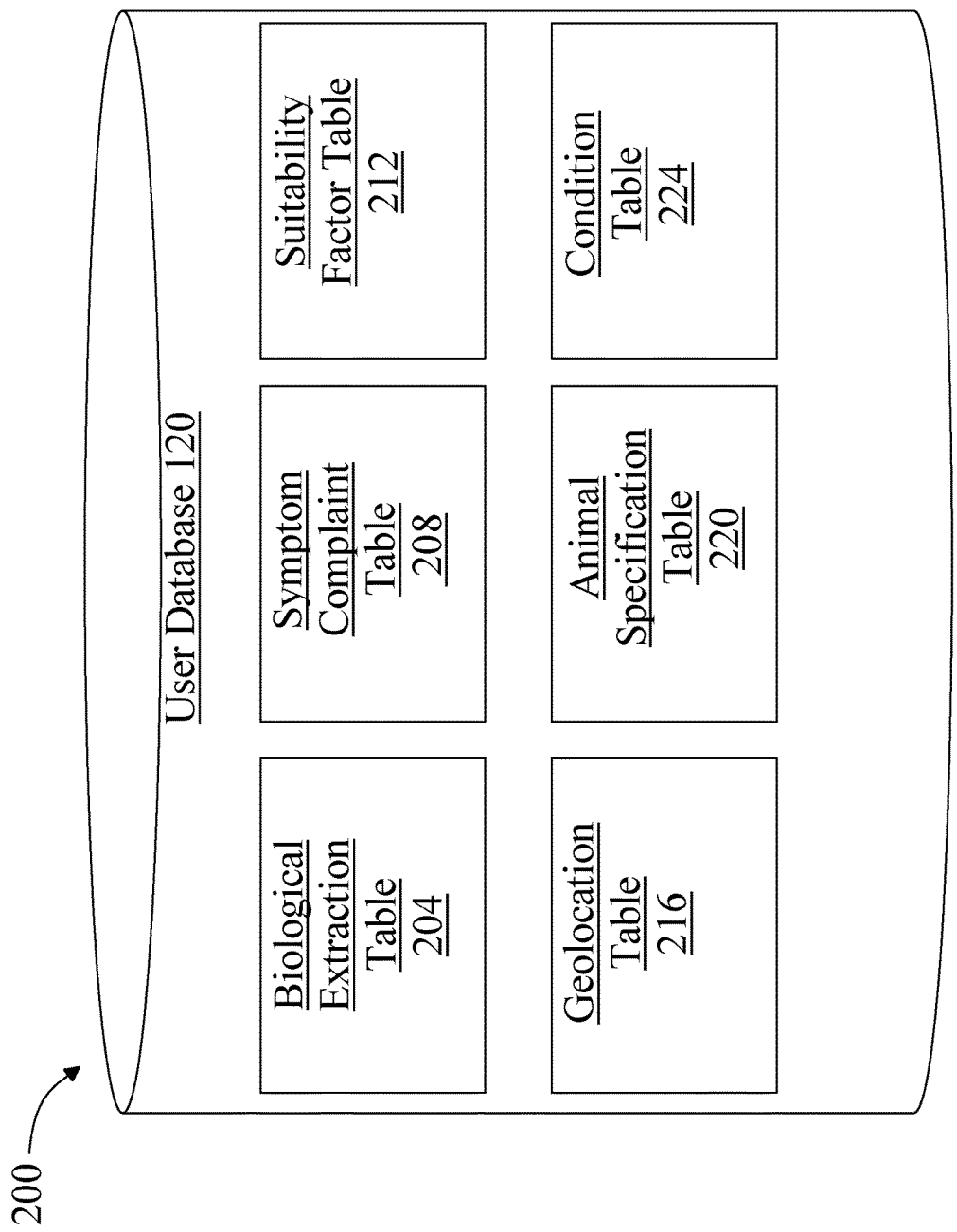
FIG. 2 is a block diagram illustrating an exemplary embodiment of a user database.

Referring now to FIG. 2, an exemplary embodiment 200 of user database 120 is illustrated. User database 120 may be implemented as any data structure as described above in more detail. One or more tables contained within user database 120 may include biological extraction table 204; biological extraction table 204 may include one or more biological extractions pertaining to a user. For instance and without limitation, biological extraction table 204 may include a first entry containing a stool sample analyzed for microbiome strains of bacteria and a second entry containing a blood sample taken from a microchip embedded under a user's skin to measure intracellular and extracellular levels of nutrients including vitamin B1, vitamin C, Vitamin D, Vitamin K, Vitamin E, and Vitamin A. One or more tables contained within user database 120 may include symptom complaint table 208; symptom complaint table 208 may include one or more user symptom complaint datum 116. For instance and without limitation, symptom complaint table 208 may include a user symptom complaint describing a user's depressed mood that includes spells of unhappiness, fatigue, and lack of energy. One or more tables contained within user database 120 may include suitability factor table 212; suitability factor table 212 may include one or more user suitability factors. For instance and without limitation, suitability factor table 212 may include information that details that the user has up to two hours per day to spend on looking after a pet, the user lives in the country and has ample space in the backyard for an animal to play, and the user is willing to spend up to $500 per month taking care of the animal. One or more tables contained within user database 120 may include geolocation table 216; geolocation table 216 may include one or more elements of user geolocation 180 data. For instance and without limitation, geolocation table 216 may include an entry that describes the user as living in Southern Florida from January through April, and living in Bangor, Me. from May through December each year. One or more tables contained within user database 120 may include animal specification 192 table 220; animal specification 192 table 220 may include one or more entries containing an animal specification 192. For instance and without limitation, animal specification table 220 may include an entry describing a user's animal specification as including any horse, any goat, and any chicken, but does not include any cats, dogs, or fish. One or more tables contained within user database 120 may include condition table 224; condition table 224 may include one or more user conditions. For instance and without limitation, condition table 224 may indicate a user was previously diagnosed with a shellfish allergy when the user was three years old and the user also suffers from osteoarthritis.

Figure 3:
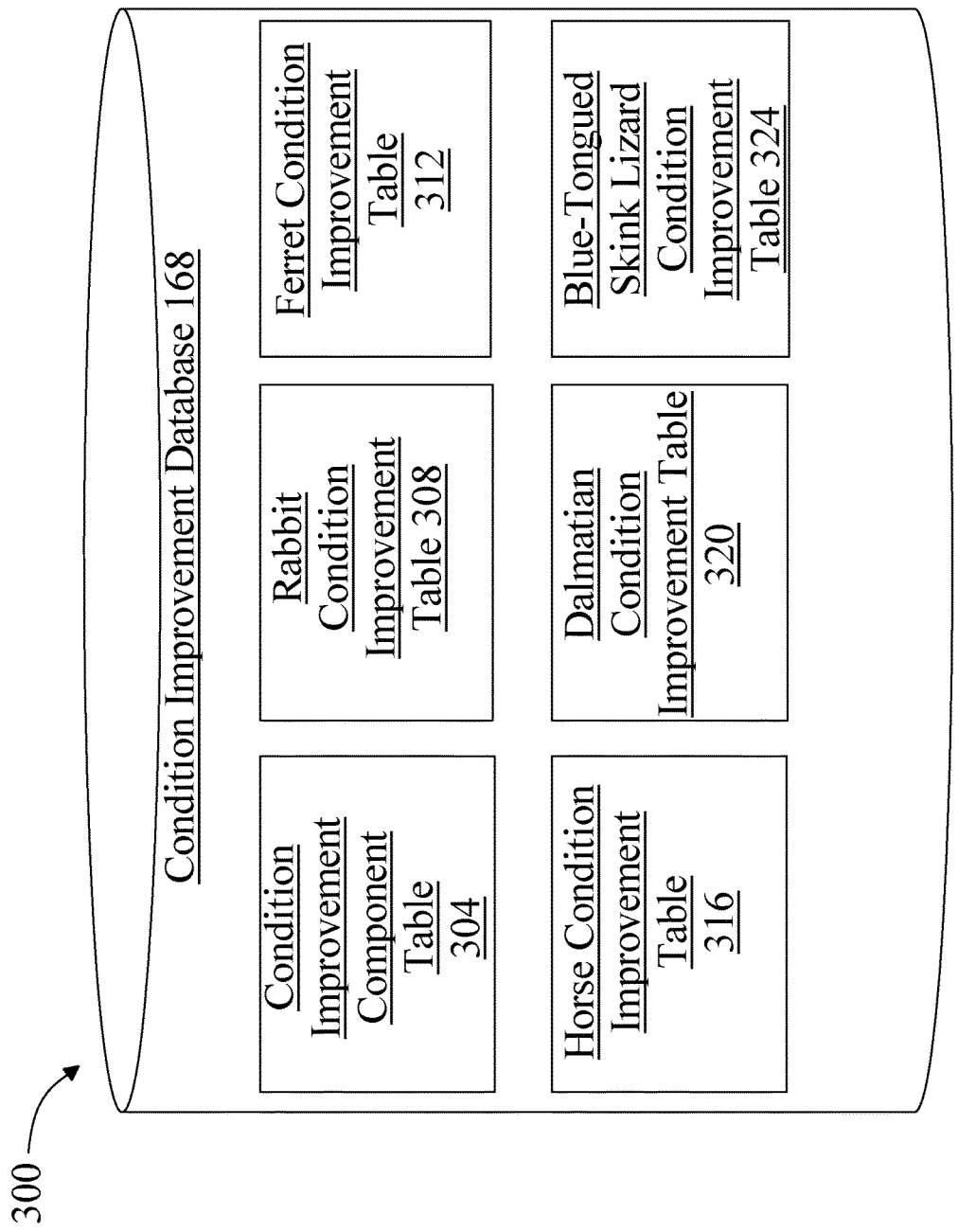
FIG. 3 is a block diagram illustrating an exemplary embodiment of a condition improvement database.

Referring now to FIG. 3, an exemplary embodiment 300 of condition improvement database 168 is illustrated. Condition improvement database 168 may be implemented as any data structure as described above in more detail. One or more tables contained within condition improvement database 168 may include condition improvement component table 304; condition improvement component table 304 may include one or more condition improvement components. For instance and without limitation, condition improvement component table 304 may include a listing of a condition such as hypertension and a condition improvement component that includes treatments such as increased activity, medication, stress reduction, meditation, and supplements. One or more tables contained within condition improvement database 168 may include rabbit condition improvement table 308; rabbit condition improvement table 308 may include condition improvements associated with having a pet rabbit. For instance and without limitation, rabbit condition improvement table 308 may indicate that having a pet rabbit reduces stress, increased opportunities for outdoor activities, and increases physical fitness. One or more tables contained within condition improvement database 168 may include ferret condition improvement table 312; ferret condition improvement table 312 may include condition improvements associated with having a pet ferret. For instance and without limitation, ferret condition improvement table 312 may indicate that having a pet ferret reduces loneliness and increases physical fitness. One or more tables contained within condition improvement database 168 may include horse condition improvement table 316; horse condition improvement table 316 may include condition improvements associated with having a pet horse. For instance and without limitation, horse condition improvement table 316 may indicate that having a pet horse increases abdominal and core strength, increases flexibility, increases muscle tone, increases energy, decreases cholesterol levels and decreases loneliness. One or more tables contained within condition improvement database 168 may include dalmatian condition improvement table 320; dalmatian condition improvement table may include condition improvements associated with having a pet dalmatian. For instance and without limitation, dalmatian condition improvement table 320 may indicate that having a pet dalmatian increases calf muscle tone, increases opportunities for socialization, increases exercise, and decreases loneliness and depression. One or more tables contained within condition improvement database 168 may include blue-tongued skin lizard condition improvement table 324; blue-tongued skin lizard condition improvement table 324 may include condition improvements associated with having a pet blue-tongued skin lizard. For instance and without limitation, blue-tongued skin lizard condition improvement table 324 may indicate that having a blue-tongued skink lizard may reduce loneliness and decrease blood pressure. Condition improvement database 168 may include condition improvements for other animals not listed in FIG. 3.

Figure 4:
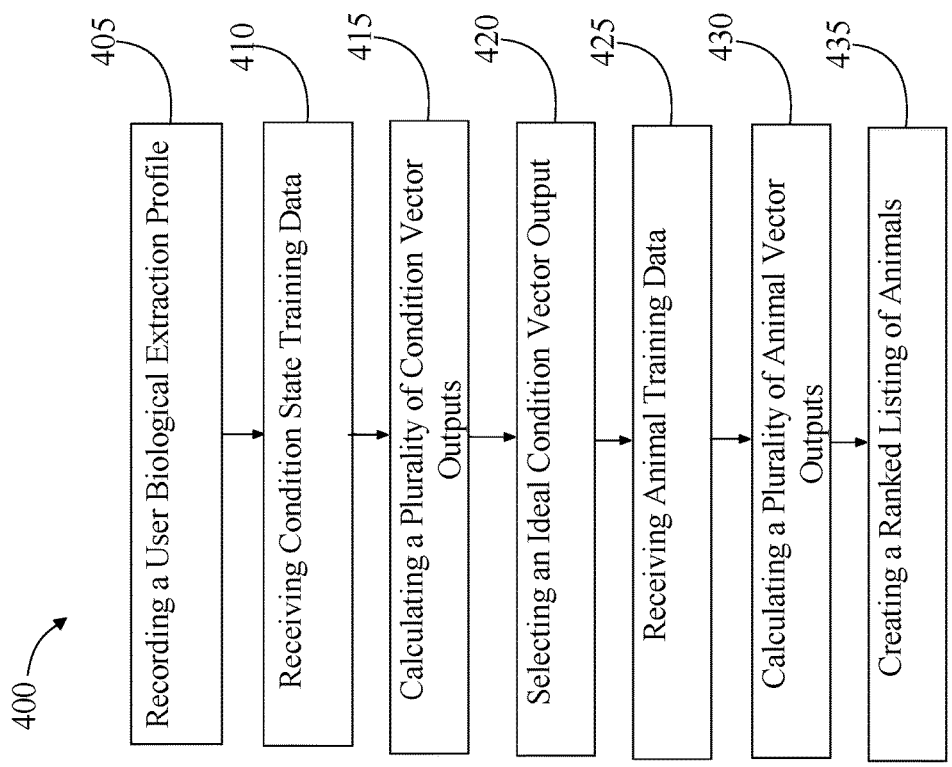
FIG. 4 is a process flow diagram illustrating an exemplary embodiment of a method of physiologically informed zoological selection.

Referring now to FIG. 4, an exemplary embodiment of a method 400 of physiologically informed zoological selection is illustrated. At step 405, a computing device 104 records a user biological extraction profile 108. A user biological extraction profile 108 includes any of the biological extraction profiles as described above in reference to FIGS. 1-3. A user biological extraction profile 108 includes at least an element of user physiological data 112 and a user symptom complaint. An element of user physiological data 112 includes any of the elements of user physiological data 112 as described above in reference to FIGS. 1-3. For instance and without limitation, an element of user physiological data 112 may include a stool sample analyzed for *Bifidobacterium* spp. levels, calprotectin levels, eosinophil protein X (EPX) levels, fecal occult blood, parasitology, triglycerides, and *Veillonella* spp. Levels. In yet another non-limiting example, an element of user physiological data 112 may include a blood sample analyzed for immunoglobulin E (IGE) and immunoglobulin G (IGG) reactions to food, mold, and spices. A user symptom complaint contains any subjective evidence of disease in a user's body as described above in more detail in reference to FIG. 1. For instance and without limitation, a user symptom complaint may describe that a user has been frequently lacking in energy, feeling sad, and not motivated to engage in social interactions. In yet another non-limiting example, a user symptom complaint may describe that a user has been feeling anxious and agitated and frequently nervous. In an embodiment, computing device 104 may receive a user symptom complaint from a remote device 144 utilizing any network methodology as described herein. In an embodiment, computing device 104 may receive a user symptom complaint from a user entry on graphical user interface 140 as described above in more detail in reference to FIG. 1.

With continued reference to FIG. 4, at step 410 computing device 104 receives condition state training data 124. Condition state training data 124 includes any of the condition state training data 124 as described above in reference to FIGS. 1-3. Condition state training data 124 includes a plurality of user biological extraction profile 108 and a plurality of correlated conditions. A condition includes any data describing the presence and/or absence of any disease, syndrome, lesion, disorder, illness, infection, epidemic, injury, and/or medical state. For instance and without limitation, condition state training data 124 may include a biological extraction profile that contains a salivary hormone panel showing increased levels of estradiol, estrone, and estriol and a correlated condition of estrogen dominance. In yet another non-limiting example, condition state training data 124 may include a biological extraction profile that contains an elevated level of anti-CdtB antibodies, and an elevated level of anti-Vinculin antibodies obtained from a stool sample and a correlated condition of irritable bowel syndrome.

With continued reference to FIG. 4, at step 415 computing device 104 calculates a plurality of condition vector output 128 for a user biological extraction profile 108 utilizing condition state training data 124 and a first clustering algorithm 132. A condition vector output 128 is a data structure representing a quantitative measure of a degree of probability of a user having a particular condition as described above in more detail in reference to FIG. 1. A condition vector output 128 may be represented in n-dimensional space. Computing device 104 calculates a plurality of condition vector output 128 using a first clustering algorithm 132. A first clustering algorithm 132 may include any of the clustering algorithms as described above in reference to FIGS. 1-3. For instance and without limitation, a first clustering algorithm 132 may include a hierarchical clustering algorithm or a density-based clustering algorithm. A first clustering algorithm 132 may include performing a series of one or more calculations. A first clustering algorithm 132 may include generating one or more clustering models.

With continued reference to FIG. 4, at step 420 computing device 104 selects a characteristic condition vector output 136 from a plurality of condition vector output 128. Computing device 104 may select an idea condition vector output 128 utilizing user input. In an embodiment, computing device 104 may receive a user input containing a specified condition. A specified condition is the identification of any condition identified as pertaining to a user identified by the user as described above in more detail in reference to FIG. 1. For instance and without limitation, a specified condition may include a user's self-report of a previous diagnosis that the user received and that is a chronic health condition. In yet another non-limiting example, a specified condition may include the identification of a condition a user believes the user suffers from because the user has experienced symptoms of the condition or many relatives in the user's family suffer from the same condition. For instance and without limitation, a user may identify a specified condition such as Type 2 Diabetes Mellites because the user's sister and mother have both been diagnosed with Type 2 Diabetes Mellitus and the user has been frequently experiencing symptoms of Type 2 Diabetes Mellites including increasing fatigue, increased thirst, and increased urination. In an embodiment, computing device 104 may receive a user input containing a specified condition from a remote device 144 operated by the user. A user input containing a specified condition may be transmitted to computing device 104 utilizing any network methodology as described herein. In an embodiment, computing device 104 may receive a user input containing a specified condition from a user entry on graphical user interface 140 located on computing device 104. Computing device 104 identifies a condition vector output 128 related to the specified condition. In an embodiment, computing device 104 may evaluate a plurality of condition vector output 128 to locate a condition vector output 128 that matches the specified condition. For instance and without limitation, computing device 104 may evaluate a plurality of condition vector output 128 to locate a condition vector output 128 that contains viral gastroenteritis that matches viral gastroenteritis contained within a specified condition.

With continued reference to FIG. 4, computing device 104 may select a characteristic condition vector output 136 utilizing a user biological extraction profile 108 vector output. In an embodiment, computing device 104 may convert a user biological extraction profile 108 to a biological extraction profile vector output. A biological extraction profile vector output includes any of the biological extraction profile vector outputs as described above in reference to FIGS. 1-3. In an embodiment, a biological extraction profile vector output may be represented in n-dimensional space. Computing device 104 maps a user biological extraction profile 108 vector output in relation to the plurality of condition vector output 128. Mapping may include measuring the distance between a user biological extraction profile 108 vector output and the plurality of condition vector output 128. Distance may be measured utilizing any of the distance measurements as described above in reference to FIG. 1. Computing device 104 locates a condition vector output 128 closest to a user biological extraction profile 108 vector output. In an embodiment, a condition vector output 128 may be closest to a user biological extraction profile 108 vector output when it measures the shortest distance. Computing device 104 selects the condition vector output 128 closest to the user biological extraction profile 108 vector output as the characteristic condition vector output.

With continued reference to FIG. 4, computing device 104 may select a characteristic condition vector output based on one or more user inputs. In an embodiment, computing device 104 may display on graphical user interface 140 a plurality of condition vector output 128. In an embodiment, computing device 104 may display on graphical user interface 140, labels indicating conditions associated with each of the plurality of vector outputs. For instance and without limitation, computing device 104 may display a plurality of labels indicating conditions for each of the plurality of condition vector output 128 that include Chron's disease, hypertension, hyperlipidemia, diabetes, back pain, anxiety, obesity, allergic rhinitis, reflux esophagitis, acute maxillary sinusitis, fibromyalgia, hypothyroidism, asthma, and nail fungus. Computing device 104 may receive a user command selecting a condition vector output 128 from a plurality of condition vector output 128. In an embodiment, a user command may indicate a selection of a vector output, and/or condition indicated by a condition vector output 128. For instance and without limitation, graphical user interface 140 may display a plurality of labels indicating conditions that include acne vulgaris, atopic dermatitis, shingles, hives, sunburn, contact dermatitis, diaper rash, and rosacea. In such an instance, a user command may indicate a selection of a vector output for acne vulgaris.

With continued reference to FIG. 4, at step 425 a computing device 104 receives zoological training data 148. Zoological training data 148 includes any of the zoological training data 148 as described above in reference to FIGS. 1-3. Zoological training data 148 includes a plurality of conditions and a plurality of correlated animals. For instance and without limitation, zoological training data 148 may include a condition such as generalized anxiety disorder (GAD), correlated to animals that include boxers, golden retrievers, huskies, Labrador retrievers, poodles, rabbits, and cats. In yet another non-limiting example, zoological training data 148 may include a condition such as coronary artery disease correlated to animals that includes any breed dog, rats, capybaras, turtles, lizards, porcupines, goats, cats, lambs, pigs, ducks, and deer.

With continued reference to FIG. 4, at step 430 a computing device 104 calculates a plurality of animal vector output 152. Animal vector output 152 include any of the animal vector output 152 as described above in reference to FIGS. 1-3. Computing device 104 may display animal vector output 152 in n-dimensional space. Computing device 104 calculates a plurality of animal vector output 152 utilizing a selected characteristic condition vector output 136, zoological training data 148 and a second clustering algorithm 156. Second clustering algorithm 156 includes any clustering algorithm suitable for use as first clustering algorithm 132. Calculating second clustering may include performing a series of one or more calculations. Calculating second clustering algorithm may include generating one or more clustering models.

With continued reference to FIG. 4, at step 435 computing device 104 creates a ranked listing of animals 160 utilizing a plurality of animal vector output 152. Ranked listing of animals 160 may identify animals in a hierarchical listing of most tolerated and/or more suitable animals to least tolerated and/or least suitable animals. In an embodiment, computing device 104 may calculate a plurality of animal vector output 152 utilizing a plurality of condition vector output 128. In an embodiment, computing device 104 may select one or more condition vector output 128 to calculate animal vector output 152. For example, a user command may indicate three conditions the user believes the user may be diagnosed with, including attention deficit hyperactivity disorder (ADHD), depression, and oppositional defiant disorder. Computing device 104 may utilize the three condition vector output 128 to generate a plurality of animal vector output 152. Computing device 104 may create a ranked listing of animals 160 as a function of a plurality of condition vector output 128. For instance and without limitation, computing device 104 may map distance between each of the plurality of condition vector output 128 and a plurality of animal vector output 152. In such an instance, computing device 104 may create a ranked listing of animals 160 based on distance measurements between each of the plurality of condition vector output 128 and each of the plurality of animal vector output 152.

With continued reference to FIG. 4, computing device 104 may create a ranked listing of animals 160 by generating one or more machine-learning algorithms. Computing device 104 may receive condition state improvement training data 164. Condition state improvement training data 164 includes a plurality of conditions and a plurality of correlated condition improvement components. Condition improvement components include data identifying any treatment that ameliorates a given condition. For instance and without limitation, condition state improvement training data 164 may include a condition such as hyperlipidemia and a correlated condition improvement component that includes aerobic exercise and reduced dietary sugar intake. In yet another non-limiting example, condition state improvement training data 164 may include a condition such as anxiety and a correlated condition improvement component that includes meditation, increased socialization, and light exercise. Computing device 104 generates a condition improvement model utilizing condition state improvement training data 164. Condition improvement model 172 includes any of the condition improvement machine-learning models as described above in reference to FIGS. 1-3. Condition improvement machine-learning model utilizes condition vectors as input and outputs condition improvement components. Computing device 104 identifies animal vectors linked to condition improvement components. In an embodiment, animal vectors may contain one or more condition improvement components associated with a particular animal vector. Computing device 104 may match an output condition improvement component generated utilizing condition improvement model 172 to one or more condition improvement components located on an animal vector. For instance and without limitation, condition improvement model 172 may output a condition improvement component such as increased physical activity for a user with a condition such as elevated fasting blood sugar. In such an instance, computing device 104 may identify animal vectors that contain condition improvement components that indicates a particular animal that increases physical activity. Computing device 104 ranks animal vectors linked to output condition improvement components. For instance and without limitation, computing device 104 may rank an animal such as a horse higher in fulfilling a condition improvement component to build core muscle strength as compared to an animal such as a dog that does not aid a user in building core muscle strength. In such an instance, computing device 104 may rank a horse as being more suitable and/or more tolerated for a user as compared to a dog.

With continued reference to FIG. 4, animals may be ranked by computing device 104 based on one or more user suitability factors. Computing device 104 may identify a user suitability factor. User suitability factor 176 includes data describing any factor that may impact a user's ability to care for and/or own an animal. For instance and without limitation, a user suitability factor 176 may indicate that a user lives on a farm and has ample space to care for large animals. In yet another non-limiting example, a user suitability factor 176 may indicate that a user only has a maximum of fifteen minutes each day to care for an animal. One or more user suitability factors may be stored in user database 120. In an embodiment, a user suitability factor 176 may be identified as a function of a user geolocation 180. For example, computing device 104 may determine that for a user who resides in Maine, a suitability factor may include one that does not require an animal to live outside all year long. In yet another non-limiting example, for a user who resides in Florida, a suitability factor may include one that requires an animal to be able to tolerate humid weather. Computing device 104 receives suitability training data. Suitability training data 184 includes a plurality of suitability factors and a plurality of correlated animals. For instance and without limitation, suitability training data 184 may include a suitability factor such as a city dweller who does not own any land and a plurality of correlated animals including a tortoise, a hare, a fish, a lizard, and a small dog. Computing device 104 generates a suitability model 188 utilizing suitability training data. Suitability model 188 may include any of the machine-learning models as described above in reference to FIGS. 1-3. Suitability model 188 may include for example, a supervised machine-learning model, an unsupervised machine-learning model, a lazy-learning model, and/or a classification model. Generating suitability model 188 may include performing a series of one or more calculations, algorithms, and/or equations. Computing device 104 maps a distance between a user suitability factor 176 and output animal vectors. Mapping a distance between a user suitability factor 176 and output animal vectors may include measuring the distance between a user suitability factor 176 and output animal vectors. Distance may be measured utilizing any of the distance measurements as described above in reference to FIGS. 1-3. Computing device 104 ranks output animal vectors as a function of the distance between a user suitability factor 176 and output animal vectors. For example, computing device 104 may rank an animal vector as being more suitable for a user if the animal vector has a shorter distance to a user suitability factor 176 as compared to a second animal vector that has a further distance to the same user suitability factor.

With continued reference to FIG. 4, computing device 104 may create a ranked listing of animals 160 based on a user request for a particular animal. Computing device 104 may receive from a remote device 144 an animal specification 192. An animal specification 192 includes data describing a user's preference for a particular animal as described above in more detail in reference to FIG. 1. For instance and without limitation, an animal specification 192 may indicate that a user would like to know the tolerability of a Siberian husky. In yet another non-limiting example, an animal specification 192 may indicate that a user would like to know the tolerability of a common basilisk lizard. Computing device 104 calculates a distance between an animal specification 192 and a plurality of animal vector output 152. Distance may be calculated utilizing any of the distance measurements as described above in reference to FIG. 1. Computing device 104 ranks an animal specification 192 within a ranked listing of animals 160 a function of distance between an animal specification and an animal vector output 152.

With continued reference to FIG. 4, computing device 104 may identify an animal of interest 196. An animal of interest 196 includes any animal that a user may seek to consider as a pet, chosen by computing device 104. Computing device 104 may identify an animal of interest 196 by generating one or more machine-learning algorithms and/or one or more machine-learning models. Machine-learning algorithms include any of the machine-learning algorithms as described above in reference to FIGS. 1-3. Machine-learning models include any of the machine-learning models as described above in reference to FIG. 1. Computing device 104 locates an animal vector output 152 related to an animal of interest 196. For example, computing device 104 may utilize an animal of interest 196 such as an African spurred tortoise to locate an animal vector output 152 intended for an African spurred tortoise. Computing device 104 determines the compatibility of an animal of interest 196 utilizing a ranked listing of animals 160. In an embodiment, computing device 104 may determine where in the ranked listing of animals 160 the animal of interest 196 fits in. In an embodiment, computing device 104 may transmit to a remote device 144 an indication as to the tolerability, ranking, and/or suitability of the identified animal of interest 196. In such an instance, transmission may occur utilizing any network methodology as described herein.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
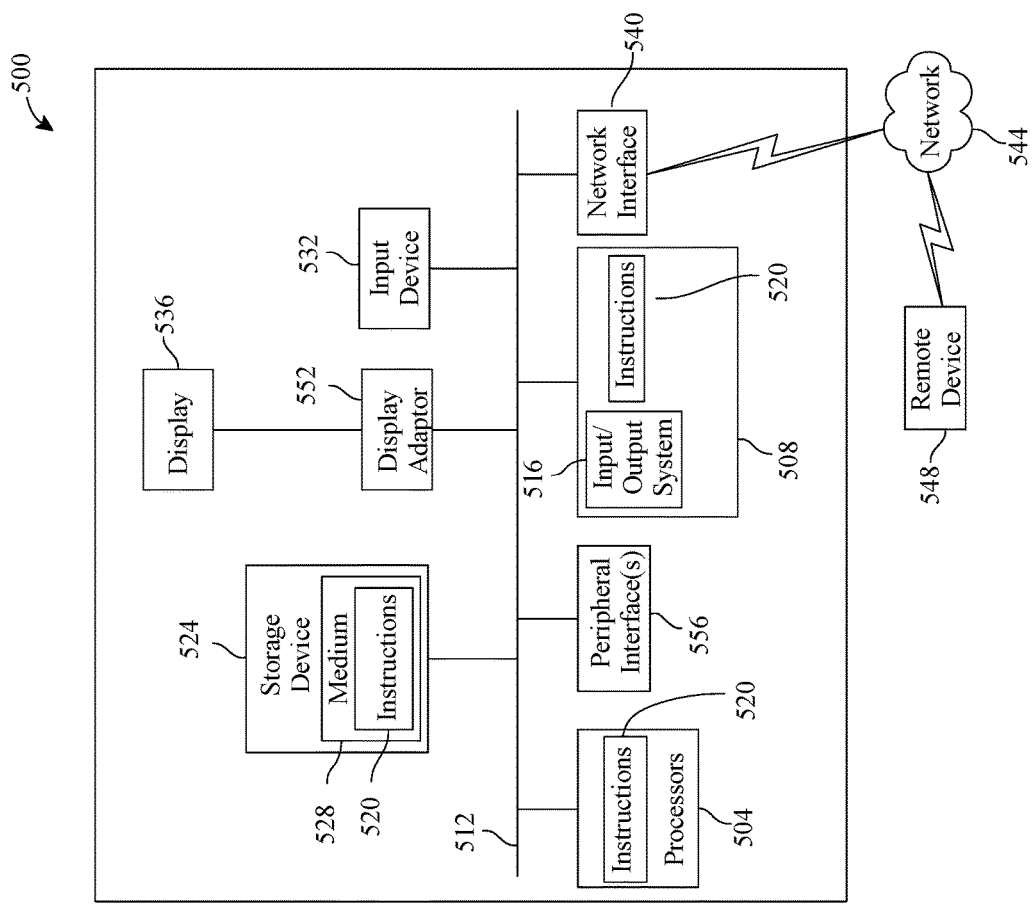
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine-readable media) including, but not limited to, a random access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote device 144 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof.

Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for physiologically informed zoological selection, the system comprising:
    a computing device, the computing device designed and configured to:
        record a user biological extraction profile wherein the user biological extraction profile contains at least an element of user physiological data and a user symptom complaint datum;
        receive condition state training data wherein condition state training data further comprises a plurality of user biological extraction profiles and a plurality of conditions correlated to the plurality of user biological extraction profiles;
        train a first clustering machine learning model utilizing the condition state training data and a first clustering algorithm;
        calculate, using the trained first clustering machine learning model, a plurality of condition vector outputs for the user biological extraction profile, wherein the user biological extraction profile is provided to the trained first clustering machine learning model as an input to output the plurality of condition vector outputs from the trained first clustering machine learning model;

select a characteristic condition vector output from the plurality of condition vector outputs;

receive zoological training data wherein zoological training data further comprises a plurality of conditions and a plurality of animals correlated to the plurality of conditions;

train a second clustering machine learning model utilizing the zoological training data and a second clustering algorithm;

calculate, using the trained second clustering machine learning model, a plurality of animal vector outputs utilizing the selected characteristic condition vector output; and create a ranked listing of animals utilizing the plurality of animal vector outputs.

2. The system of claim 1, wherein the computing device is further configured to:

receive a user input containing a specified condition; and identify a condition vector output of the plurality of condition vector outputs related to the specified condition.

3. The system of claim 1, wherein the computing device is further configured to:

convert the user biological extraction profile to a user biological extraction profile vector output;

map the user biological extraction profile vector output in relation to the plurality of condition vector outputs;

locate a condition vector output of the plurality of condition vector outputs closest to the user biological extraction profile vector output; and select the condition vector output closest to the user biological extraction profile vector output as the characteristic condition vector output.

4. The system of claim 1, wherein the computing device is further configured to:

display, on a graphical user interface located on the computing device, the plurality of condition vector outputs; and receive, a user command selecting a condition vector output from the plurality of condition vector outputs.

5. The system of claim 1, wherein the computing device is further configured to:

calculate the plurality of animal vector outputs utilizing the plurality of condition vector outputs; and create a ranked listing of animals as a function of the plurality of condition vector outputs.

6. The system of claim 1, wherein the computing device is further configured to:

receive condition state improvement training data wherein condition state improvement training data further comprises a plurality of conditions and a plurality of correlated condition improvement components;

generate a condition improvement model utilizing the condition state improvement training data wherein the condition improvement model utilizes condition vectors as an input and outputs condition improvement components;

identify animal vectors of the plurality of animal vector outputs linked to output condition improvement components; and rank the identified animal vectors linked to the output condition improvement components.

7. The system of claim 1, wherein the computing device is further configured to:

identify a user suitability factor;

receive suitability training data wherein the suitability training data further comprises a plurality of suitability factors and a plurality of correlated animals;

generate a suitability model utilizing the suitability training data wherein the suitability model utilizes suitability factors as an input and outputs animal vectors;

map the distance between the user suitability factor and output animal vectors of the plurality of animal vector outputs; and rank the output animal vectors as a function of the distance between the user suitability factor and the output animal vectors.

8. The system of claim 7, wherein the computing device is further configured to identify the user suitability factor as a function of a user geo-location.

9. The system of claim 1, wherein the computing device is configured to create the ranked listing of animals by:

receiving, from a remote device, at least an animal specification;

calculating a distance between the at least an animal specification and the plurality of animal vector outputs; and ranking the at least an animal specification within the ranked listing of animals as a function of the distance.

10. The system of claim 1, wherein the computing device is further configured to:

identify an animal of interest;

locate an animal vector output of the plurality of animal vector outputs related to the animal of interest; and determine the compatibility of the animal of interest utilizing the ranked listing of animals.

11. A method of physiologically informed zoological selection, the method comprising:

recording by a computing device a user biological extraction profile wherein the user biological extraction profile contains at least an element of user physiological data and a user symptom complaint datum;

receiving by the computing device condition state training data wherein condition state training data further comprises a plurality of user biological extraction profiles and a plurality of conditions correlated to the plurality of user biological extraction profiles;

training by the computing device a first clustering machine learning model utilizing the condition state training data and a first clustering algorithm;

calculating, using the trained first clustering machine learning model, by the computing device a plurality of condition vector outputs for the user biological extraction profile, wherein the user biological extraction profile is provided to the trained first clustering machine learning model as an input to output the plurality of condition vector outputs from the trained first clustering machine learning model;

selecting by the computing device a characteristic condition vector output from the plurality of condition vector outputs;

receiving by the computing device zoological training data wherein zoological training data further comprises a plurality of conditions and a plurality of animals correlated to the plurality of conditions;

training by the computing device a second clustering machine learning model utilizing the zoological training data and a second clustering algorithm;

calculating by the computing device, utilizing the second trained clustering machine learning model, a plurality of animal vector outputs utilizing the selected characteristic condition vector output; and creating by the computing device a ranked listing of animals utilizing the plurality of animal vector outputs.

12. The method of claim 11, wherein selecting the characteristic condition vector output further comprises:
receiving a user input containing a specified condition; and
identifying a condition vector output of the plurality of condition vector outputs related to the specified condition.

13. The method of claim 11, wherein selecting the characteristic condition vector output further comprises:
converting the user biological extraction profile to a biological extraction profile vector output;
mapping the user biological extraction profile vector output in relation to the plurality of condition vector outputs;
locating a condition vector output of the plurality of condition vector outputs closest to the user biological extraction profile vector output; and
selecting the condition vector output closest to the user biological extraction profile vector output as the characteristic condition vector output.

14. The method of claim 11, wherein selecting the characteristic condition vector output further comprises:
displaying, on a graphical user interface located on the computing device, the plurality of condition vector outputs; and
receiving, a user command selecting a condition vector output from the plurality of condition vector outputs.

15. The method of claim 11, wherein creating the ranked listing of animals further comprises:
calculating the plurality of animal vector outputs utilizing the plurality of condition vector outputs; and
creating a ranked listing of animals as a function of the plurality of condition vector outputs.

16. The method of claim 11, wherein creating the ranked listing of animals further comprises:
receiving condition state improvement training data wherein condition state improvement training data further comprises a plurality of conditions and a plurality of correlated condition improvement components;
generating a condition improvement model utilizing the condition state improvement training data wherein the condition improvement model utilizes condition vectors as an input and outputs condition improvement components;
identifying animal vectors of the plurality of animal vector outputs linked to output condition improvement components; and
ranking the identified animal vectors linked to the output condition improvement components.

17. The method of claim 11, wherein creating the ranked listing of animals further comprises:
identifying a user suitability factor;
receiving suitability training data wherein the suitability training data further comprises a plurality of suitability factors and a plurality of correlated animals;
generating a suitability model utilizing the suitability training data wherein the suitability model utilizes suitability factors as input and outputs animal vectors;
mapping the distance between the user suitability factor and output animal vectors of the plurality of animal vector outputs; and
ranking the output animal vectors as a function of the distance between the user suitability factor and the output animal vectors.

18. The method of claim 17, wherein the user suitability factor is identified as function of a user geo-location.

19. The method of claim 11, wherein creating the ranked listing of animals further comprises:
receiving, from a remote device, at least an animal specification;
calculating a distance between the at least an animal specification and the plurality of animal vector outputs; and
ranking the at least an animal specification within the ranked listing of animals as a function of the distance.

20. The method of claim 11 further comprising:
identifying an animal of interest;
locating an animal vector output of the plurality of animal vector outputs related to the animal of interest; and
determining the compatibility of the animal of interest utilizing the ranked listing of animals.

* * * * *